United States Patent [19]

Hecker

[11] Patent Number: 6,123,477
[45] Date of Patent: Sep. 26, 2000

[54] DEVICE AND METHOD FOR DISINFECTING THE BRUSH HEADS OF TOOTHBRUSHES

[76] Inventor: Frithjof Hecker, Ruebkerstrasse 6c, Buxtehude 21614, Germany

[21] Appl. No.: 09/202,647

[22] PCT Filed: Jun. 11, 1997

[86] PCT No.: PCT/EP97/03030

§ 371 Date: Dec. 18, 1998

§ 102(e) Date: Dec. 18, 1998

[87] PCT Pub. No.: WO97/49316

PCT Pub. Date: Dec. 31, 1997

[30]     Foreign Application Priority Data

Jun. 25, 1996 [DE] Germany .................... 196 25 314

[51] Int. Cl.⁷ ................ A46B 11/02; A61L 2/18
[52] U.S. Cl. ............... 401/186; 15/105; 206/209.1; 401/183; 401/205; 401/268; 401/270; 401/287; 401/291; 28/292; 422/28; 422/292
[58] Field of Search ................ 401/129, 137, 401/183–186, 268, 270, 278, 287, 291, 205; 422/28, 292; 15/105, 106; 206/209.1

[56]     References Cited

U.S. PATENT DOCUMENTS

| | | | |
|---|---|---|---|
| 3,345,673 | 10/1967 | Schwartzman | 401/183 |
| 3,605,160 | 9/1971 | Maurer | 15/105 |
| 4,850,729 | 7/1989 | Kramer et al. | 401/183 |
| 4,995,509 | 2/1991 | Kornfeind | 206/209.1 |
| 5,922,292 | 7/1999 | Hecker et al. | 422/300 |

FOREIGN PATENT DOCUMENTS

| | | |
|---|---|---|
| 19606136 | 8/1997 | Germany . |
| 2232581 | 12/1990 | United Kingdom . |
| 2252908 | 8/1992 | United Kingdom . |

*Primary Examiner*—Henry J. Recla
*Assistant Examiner*—Kathleen J. Prunner
*Attorney, Agent, or Firm*—Pearne & Gordon LLP

[57]     ABSTRACT

In a method for disinfecting the brush head of a toothbrush, disinfecting bristles (20, 200) are mounted on a substrate and are wetted with a disinfectant (15). The wetted disinfecting bristles are inserted between toothbrush bristles (17) of a toothbrush head (11) and maintained between the toothbrush bristles for a time selected to disinfect the toothbrush bristles. The bristles can be inserted between the toothbrush bristles dry and subsequently wetted with the disinfectant. An apparatus for performing the method is disclosed.

1 Claim, 2 Drawing Sheets

DEVICE AND METHOD FOR DISINFECTING THE BRUSH HEADS OF TOOTHBRUSHES

FIELD OF THE INVENTION

The present invention relates to apparatus and a method for disinfecting toothbrush heads with liquid disinfectants.

BACKGROUND OF THE INVENTION

The use of toothbrushes incurs the problem that the brush heads are contaminated during teeth cleaning with bacteria or viruses present in the oral cavity. As long as the brush is not fully dried, the ambient conditions of the brush head suffice for germ survival. Because the toothbrush bristles are arranged tightly against each other, the liquid absorbed by them during tooth brushing is stored for a comparatively long time in the brush head. If the toothbrush is used twice daily, or, as recommended by the professionals, possibly three times, then it must be assumed that full drying of the brush head—which in air takes approximately 72 hours—will not take place.

Accordingly, the toothbrush remains contaminated when used typically and therefore it must be presumed that in each brushing germs are reintroduced into the mouth. Self-infection may then take place in extant malady. Moreover the repeated spreading of pathogenic bacteria by the toothbrush in the mouth caused by bacterial odontopathies is undesired. The situation is more critical still when the toothbrush is used not by one person, but by several different ones, or when individually used toothbrushes are so kept in a common vessel that contact and hence pathogen exchange is possible between the brushes. In such cases the undesired self-infection is made more acute by the infection from foreign germs.

Accordingly it has already been proposed to disinfect the brush head between brushings. Illustratively, cleansing apparatus for toothbrush heads are already known from Japanese patent document 3-167 139 and from German Gebrauchsmuster 91 07 132.1, in which sterilization is implemented using hot air or steam in the absence of sterilizing means.

Apparatus of this species, disclosed in the German patent document 296 02 929 U1, consists of a container of one or several compartments and fitted with a lid, the compartments being filled with liquid disinfectants. Between brushings, the toothbrushes are individually placed in the compartments, a comb present in the lid wiping the brush head being inserted and removing coarse particles from the head's bristles. It is questionable whether in such apparatus all zones, that is including the lowermost bristle zones, which are known to be the least accessible and the slowest to dry, are in fact reached by the disinfectant. Moreover, there is danger that the disinfectant's effectiveness will degrade several hours after its application. Again, the fairly long time intervals spent by the toothbrush in the solution between brushings are considered unsanitary.

SUMMARY OF THE INVENTION

Therefore, it is an object of the invention to create an apparatus and a method for disinfecting toothbrush heads, wherein also the critical inner zones of the brush heads are easily reached and can be reliably treated.

The invention applies in general to a method for disinfecting the brush heads of toothbrushes in which disinfection brush bristles are wetted with a disinfectant and the wetted disinfection bristles then are inserted between the brush head bristles to be disinfected. In the simplest case, this method can be implemented using a row of conventional pencil brushes with appropriately rigid disinfection bristles. However, other substrates fitted with suitable disinfection bristles also are applicable. Again, the disinfection bristles may be initially inserted into those of the toothbrush head before the disinfectant is actively introduced, that is, while pressurized.

The disinfectants may be the substances used in contemporary mouthwashes. Obviously all other bodily compatible disinfectants such as chlorohexidine, alexidine, benzoic acid, thymol, menthol or spirits also may be used.

The apparatus of the invention comprises a container, which where desired may be refillable, for a liquid disinfectant. A special device to introduce disinfectant into the brush head is connected to an orifice of this container. This device is fitted with disinfection bristles projecting from a liquid-permeable substrate and thereby is connected in such manner with the container orifice that the liquid-permeable substrate can be loaded with disinfectant from the container on a side away from the disinfection bristles. Preferably, the disinfection bristles of the invention are made of plastic and of such materials that can be wetted well and permanently with liquids and offer good flow properties.

In the disinfection procedure of the invention, the disinfection bristles of the apparatus of the present invention are first wetted with disinfectant from the container and then are inserted into the brush head. To also reach the base of the brush head, the disinfection bristles of the apparatus of the invention must be at least as long as the bristles of the treated toothbrush, though advantageously slightly longer. The disinfection bristles of the apparatus of the invention spread apart the brush head bristles and the disinfectant adhering to the apparatus' disinfection bristles easily arrives as far as the toothbrush bristles' base. The diameter and stiffness of the disinfection bristles of the apparatus of the invention are selected so that, on one hand, they easily spread apart the always bunched toothbrush bristles and that, on the other hand, they can move the disinfectant also into the regions of the brush head which are most difficult to access. Conceivably too, the apparatus' disinfection bristles may be first inserted in a dry condition in the brush head and then be loaded with disinfectant. Even in such a case the disinfectant would be fairly well spread inside the brush head especially on account of capillary effect. Preferably however, and as discussed above, the disinfection bristles of the apparatus of the invention are loaded with liquid disinfectant before being inserted into the brush head and then individually make contact as disinfecting surfaces with the mating surfaces in the brush head.

Accordingly, the apparatus of the invention makes possible simple and exhaustive disinfection of a toothbrush's brush head. Moreover the disinfection bristles of the apparatus of the invention also can be used, before disinfection proper, to remove contaminations from the brush, and in such a case cleaning is carried out in addition to the primary purpose.

Advantageously, the device of the invention is a brush of which the base substantially covers the orifice of the disinfectant container, the base being fitted with an adequate number of perforations to wet the disinfection bristles. A simple design consists in particular of the brush being connected, for instance by screwing, on the container.

Moreover the walls of the disinfectant-filled container may consist at least in some zones of a deformable material. In such a design the container is compressible and the liquid can be actively forced into the disinfection bristles of the connected device.

In this respect, furthermore, the container may be shaped in such manner that it easily can be seized manually. In that case the toothbrush may easily be held in one hand while disinfection or cleaning of the brush head is carried out with the other hand.

As already discussed above, the apparatus of the invention operates best if first the disinfection bristles are wetted with liquid disinfectant and then are inserted into the brush head. This procedures has two simultaneous advantages. The first advantage is that the disinfection bristles of the apparatus of the invention spread the bristles of the brush head apart and then can effortlessly penetrate the brush head to its innermost portion. If the disinfection bristles of the apparatus of the invention already were fully wetted with disinfectant before insertion, then each bristle constitutes a sort of plunger or swab disinfecting all areas it makes contact with while entering the toothbrush head. When the disinfection bristles of the apparatus of the invention are correspondingly selected regarding length, number etc., the presumption is justified that all the toothbrush head bristles are in contact with the disinfectant over their entire surface. Another advantage is that in comparison with the known bath of solution or the also known spray disinfection outside the scope of this invention, substantially less disinfectant is required for the desired effect. Therefore the user enjoys both economical and health relief.

BRIEF DESCRIPTION OF THE DRAWINGS

The invention is described below with reference to two drawings of illustrative embodiments of the invention.

DESCRIPTION OF PREFERRED EMBODIMENTS

Figure 1:
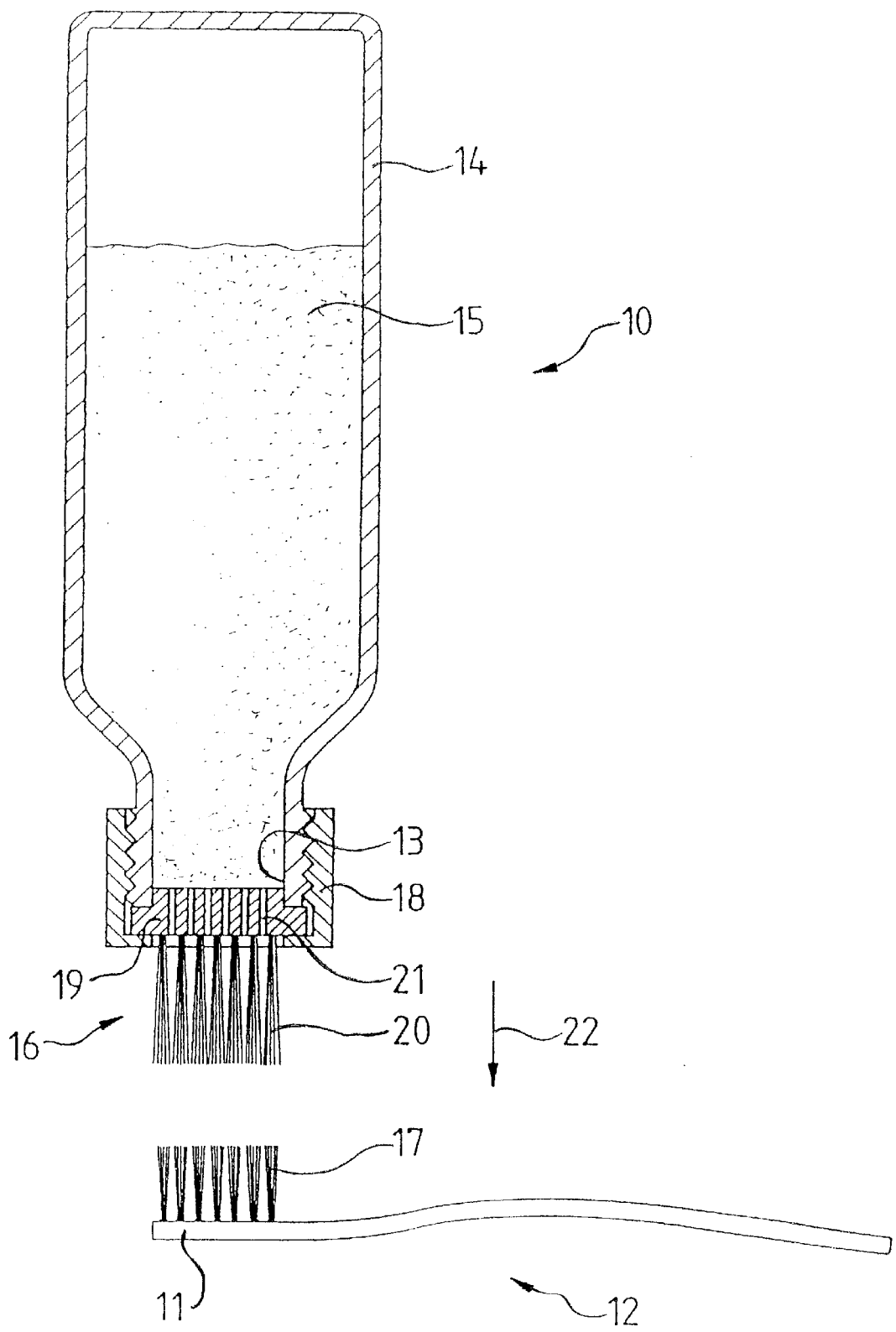
FIG. 1 shows an illustrative embodiment of the apparatus of the invention before being inserted in the brush head of a toothbrush.

FIG. 1 shows an overhead arrangement of an apparatus 10 to disinfect a brush head 11 of a toothbrush 12. The apparatus 10 comprises a container 14 fitted with an orifice 13 and filled with a liquid disinfectant 15. A device 16 is set into orifice 13 and is used to load liquid disinfectant 15 present in container 14 into bristles 17 of brush head 11. For that purpose device 16 is fitted with a base 19 attachable by a threaded collar 18 on container orifice 13, with disinfection bristles 20 outwardly projecting from base 19. Base 19 is fitted with perforations 21 allowing liquid disinfectant 15 to pass through base 19 into disinfection bristles 20.

As already discussed above, disinfection bristles 20 are initially and fully wetted with liquid disinfectant 15 from container 14 before disinfecting brush head 11. Thereupon, apparatus 10 is moved in the direction of arrow 22 with its disinfection bristles 20 entering bristles 17 of toothbrush head 11. In the process, bristles 17 are spread apart and are disinfected over their full surfaces by disinfection bristles 20 wetted with disinfectant 15 of apparatus 10 of the invention.

Alternatively, disinfection bristles 20 of apparatus 10 may be initially inserted into bristles 17 of head 11 and disinfectant 15 may be subsequently applied. Presumably, adequate spreading of the disinfectant in the bristles 17—especially by capillarity—would then take place. But a more reliable procedure—as already emphasized above—is to first wet disinfection bristles 20 of apparatus 10 of the invention with liquid disinfectant and then to move them into contact with bristles 17 of brush head 11.

As already discussed above, container 14 may be fitted with deformable walls allowing expelling liquid disinfectant 15.

Figure 2:
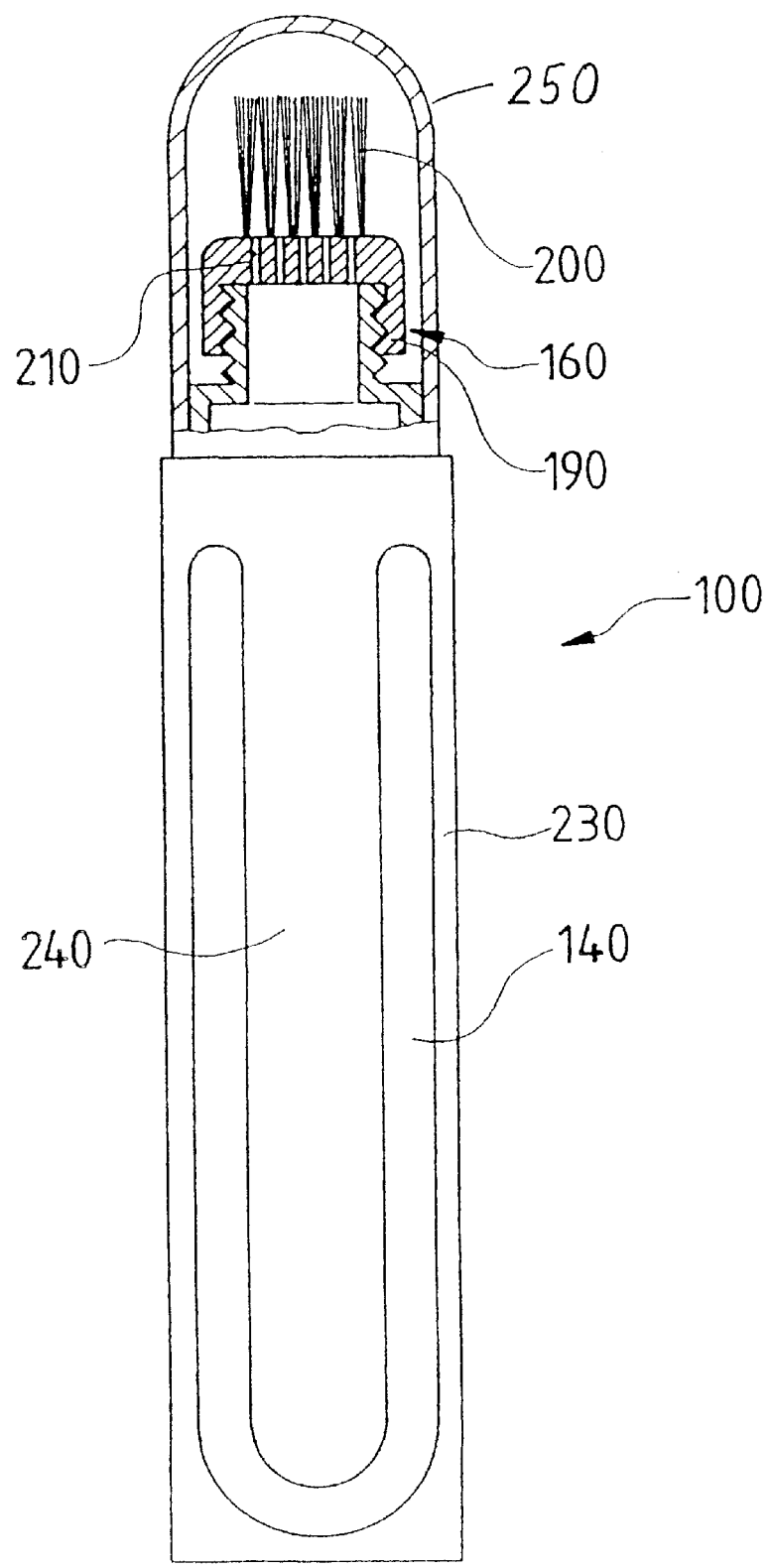
FIG. 2 shows another embodiment.

FIG. 2, in this respect, shows a further embodiment 100 of the apparatus of the invention. It comprises a container 140 receiving a liquid disinfectant. A device 160 is screwed onto the orifice-side of container 140 and corresponds substantially to the device 16 of FIG. 1. In this embodiment, disinfection bristles 200 project from a base 190 perforated with holes 210. In principle, this apparatus operates just like that described in relation to FIG. 1. In addition there is a cap 250 which can be put in place on container 140 between use. The main difference from the apparatus shown in FIG. 1 is that the walls of container 140 are made of a deformable material. For stabilization, container 140 is seated in a case 230 fitted with mutually opposite leaf springs 240 or the like (in the Figure, only the leaf spring facing the observer is shown). If now liquid disinfectant is to be expelled from container 140, then leaf springs 240 only have to be compressed. Similarly (as described in relation to FIG. 1), disinfection bristles 200 of device 160 can then be wetted and be inserted into a brush head of a toothbrush.

What is claimed is:

1. A method for disinfecting the brush head of a toothbrush comprising the steps of providing a plurality of disinfecting bristles (20, 200) mounted on a substrate, inserting the disinfecting bristles (20, 200) between toothbrush bristles (17) of a toothbrush head (11), introducing through the substrate onto the disinfecting bristles a quantity of liquid disinfectant sufficient to disinfect the toothbrush bristles, and maintaining the disinfecting bristles between the toothbrush bristles for a time selected to disinfect the toothbrush bristles.

* * * * *